United States Patent
Ilekti et al.

(10) Patent No.: US 10,568,815 B2
(45) Date of Patent: *Feb. 25, 2020

(54) COMPOSITION COMPRISING STABILIZED POLYMER PARTICLES AND A HYDROPHOBIC FILM-FORMING POLYMER

(71) Applicant: L'OREAL, Paris (FR)

(72) Inventors: Philippe Ilekti, Chevilly Larue (FR); Laure Daubersies, Chevilly Larue (FR); Nathalie Gavache, Orleans (FR); Stephane Douezan, Le Kremlin Bicetre (FR)

(73) Assignee: L'OREAL, Paris (FR)

( * ) Notice: Subject to any disclaimer, the term of this patent is extended or adjusted under 35 U.S.C. 154(b) by 58 days.

This patent is subject to a terminal disclaimer.

(21) Appl. No.: 15/537,409

(22) PCT Filed: Dec. 18, 2015

(86) PCT No.: PCT/EP2015/080629
§ 371 (c)(1),
(2) Date: Jun. 26, 2018

(87) PCT Pub. No.: WO2016/097361
PCT Pub. Date: Jun. 23, 2016

(65) Prior Publication Data
US 2019/0091116 A1   Mar. 28, 2019

(30) Foreign Application Priority Data

Dec. 18, 2014 (FR) ...................... 14 62731

(51) Int. Cl.
| A61K 8/04 | (2006.01) |
| A61Q 1/10 | (2006.01) |
| A61K 8/31 | (2006.01) |
| A61K 8/81 | (2006.01) |
| A61K 8/92 | (2006.01) |
| A61Q 1/00 | (2006.01) |

(52) U.S. Cl.
CPC .................. *A61K 8/04* (2013.01); *A61K 8/31* (2013.01); *A61K 8/8111* (2013.01); *A61K 8/8117* (2013.01); *A61K 8/8152* (2013.01); *A61K 8/92* (2013.01); *A61Q 1/00* (2013.01); *A61Q 1/10* (2013.01)

(58) Field of Classification Search
CPC .......... A61Q 1/00; A61Q 1/10; A61K 8/8111; A61K 8/31; A61K 8/8152; A61K 8/92; A61K 8/04

See application file for complete search history.

(56) References Cited

U.S. PATENT DOCUMENTS

| 4,887,622 A | 12/1989 | Gueret |
| 5,221,534 A | 6/1993 | DesLauriers et al. |
| 5,492,426 A | 2/1996 | Gueret |
| 5,928,632 A | 7/1999 | Reusch |
| 5,945,095 A * | 8/1999 | Mougin .................. A61K 8/04 424/450 |
| 6,153,206 A | 11/2000 | Anton et al. |
| 2002/0055562 A1 | 5/2002 | Butuc |
| 2004/0156812 A1 | 8/2004 | Lion |
| 2006/0099164 A1 | 5/2006 | De La Poterie et al. |
| 2006/0193803 A1 | 8/2006 | Farcet |
| 2007/0041920 A1* | 2/2007 | Blin ..................... A61K 8/8111 424/64 |

(Continued)

FOREIGN PATENT DOCUMENTS

| BR | PI0405758-9 A | 9/2006 |
| CN | 1513886 A | 7/2004 |

(Continued)

OTHER PUBLICATIONS

Griffin, "Calculation of HLB Values of Non-Ionic Surfactants", Journal of Cosmetic Science, vol. 5, No. 4, Jan. 1954, pp. 249-256.
Office Action for JP Pat. Appln. No. 2017-532866 with English Translation dated Apr. 23, 2018.
International Search Report for PCT/EP2015/080629 (4 pages) dated Feb. 22, 2016.
Written Opinion for PCT/EP2015/080629 (5 pages) dated Feb. 22, 2016.
Database GNPD [Online] Mintel; Sep. 1, 2014 "Lip Stick", XP002742990, Database Accession No. 2652869.
Database GNPD [Online] Mintel; Mar. 1, 2011 "Rouge d'Armani Lasting Satin Lip Color", XP002742991, Database Accession No. 1526500.

(Continued)

*Primary Examiner* — Jianfeng Song
(74) *Attorney, Agent, or Firm* — Shumaker, Loop & Kendrick, LLP

(57) ABSTRACT

The present invention relates to a composition, especially a cosmetic composition, for caring for and/or making up keratin materials, comprising at least: a non-aqueous medium containing at least one hydrocarbon-based oil, particles of at least one polymer that is surface-stabilized with a stabilizer, the polymer of the particles being a $C_1$-$C_4$ alkyl (meth) acrylate polymer; the stabilizer being an isobornyl (meth)acrylate polymer chosen from isobornyl (meth) acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; and a hydrophobic film-forming polymer chosen from block ethylenic copolymers and hydrocarbon-based resins, and. mixtures thereof. The present invention also relates to a cosmetic process for making up and/or caring for keratin materials, and to the use of a dispersion of particles of at least one polymer that is surface-stabilized with a stabilizer in a non-aqueous medium containing at least one hydrocarbon-based oil, for preparing a mascara or eyeliner composition.

14 Claims, No Drawings

(56) References Cited

U.S. PATENT DOCUMENTS

| | | | |
|---|---|---|---|
| 2007/0104667 A1 | 5/2007 | Mondet et al. | |
| 2007/0212317 A1 | 9/2007 | Atis et al. | |
| 2008/0026445 A1 | 1/2008 | Chisholm et al. | |
| 2010/0178257 A1 | 7/2010 | Farcet | |
| 2011/0002864 A1 | 1/2011 | Ilekti et al. | |
| 2011/0020263 A1 | 1/2011 | Ilekti et al. | |
| 2011/0243864 A1* | 10/2011 | Farcet | A61K 8/04 424/61 |
| 2013/0171084 A1* | 7/2013 | Kawaratani | A61K 8/89 424/64 |
| 2016/0175204 A1 | 6/2016 | El-Khouri et al. | |
| 2016/0175205 A1 | 6/2016 | Debeaud et al. | |
| 2016/0175230 A1 | 6/2016 | Halpern Chirch et al. | |
| 2016/0175231 A1 | 6/2016 | Halpern Chirch et al. | |
| 2016/0175232 A1 | 6/2016 | El-Khouri et al. | |
| 2016/0184211 A1 | 6/2016 | Debeaud et al. | |
| 2016/0317423 A1 | 11/2016 | Portal et al. | |

FOREIGN PATENT DOCUMENTS

| | | |
|---|---|---|
| CN | 1868444 A | 8/2006 |
| CN | 101926748 A | 12/2010 |
| EP | 1411069 A2 | 4/2004 |
| EP | 1674076 A2 | 6/2006 |
| FR | 2722380 A1 | 7/1999 |
| FR | 2792618 A1 | 10/2000 |
| FR | 2761959 A1 | 1/2001 |
| FR | 2796529 A1 | 1/2001 |
| FR | 2863493 A1 | 6/2005 |
| FR | 2937645 A1 | 4/2010 |
| FR | 2951641 A1 | 4/2011 |
| FR | 2972630 A1 | 9/2012 |
| FR | 2972631 A1 | 9/2012 |
| JP | 2005112834 A | 4/2005 |
| JP | 2005-126417 A | 5/2005 |
| JP | 2006-503922 A | 2/2006 |
| JP | 2006-510734 A | 3/2006 |
| JP | 2006510734 A | 3/2006 |
| JP | 2006213717 A | 8/2006 |
| JP | 2007-506708 A | 3/2007 |
| JP | 2009-242340 A | 10/2009 |
| JP | 2014-125428 A | 7/2014 |
| KR | 10-0231637 B1 | 11/1999 |
| WO | 199962497 A1 | 12/1999 |
| WO | 199965455 A1 | 12/1999 |
| WO | 2004/055080 A2 | 7/2004 |
| WO | 2008081175 A2 | 7/2008 |
| WO | 2008155059 A2 | 12/2008 |
| WO | 2011/148328 A2 | 12/2011 |
| WO | 2013/190133 A2 | 12/2013 |
| WO | 2013190702 A1 | 12/2013 |
| WO | 2016096660 A1 | 6/2016 |
| WO | 2016100821 A1 | 6/2016 |

OTHER PUBLICATIONS

International Search Report for PCT/EP2015/080607 (3 pages) dated Feb. 24, 2016.

Written Opinion for PCT/EP2015/080607 (6 pages) dated Feb. 24, 2016.

International Search Report for PCT/EP2015/080619 (2 pages) dated Feb. 19, 2016.

Written Opinion for PCT/EP2015/080619 (6 pages) dated Feb. 19, 2016.

Office Action dated Nov. 30, 2018 in U.S. Appl. No. 15/537,423 (50 pages).

Semchikov Y.D., 2003 (3 pages). (cited in Nov. 30, 2018 Office Action for Russian Patent Application No. 2017120489/04(035544) with the translation provided herein, which serves as a concise statement of relevance per MPEP 609.04(a)(III)).

Translation of Office Action dated Nov. 30, 2018 in Russian Patent Application No. 2017120489/04(035544) (6 pages).

* cited by examiner

COMPOSITION COMPRISING STABILIZED POLYMER PARTICLES AND A HYDROPHOBIC FILM-FORMING POLYMER

TECHNICAL FIELD AND BACKGROUND OF THE INVENTION

The present invention relates to the field of caring for and/or making up keratin materials and/or keratin fibres, and is directed towards proposing compositions more particularly intended for making up the eyelashes and the contours of the eyelids or the eyes.

The term "keratin materials" preferably means human keratin materials, especially keratin fibres.

The term "keratin fibres" in particular means the eyelashes and/or the eyebrows, and preferably the eyelashes. For the purposes of the present invention, this term "keratin, fibres" also extends to synthetic false eyelashes.

The present invention proves to be most particularly advantageous for caring for and/or making up keratin materials.

In general, compositions intended for making up keratin fibres (mascara), for example the eyelashes, or for coating the skin (liner), for example the contour of the eyes or the eyelids (eyeliner) or the lips (lip liner), are of a nature which affords a matt makeup effect. The reason for this is that it is difficult to give them a capacity to afford a glossy film, given the lack of compatibility of the compounds conventionally considered for this purpose, in the field of making up the lips or the nails, and given the implementation imperatives required for making up the eyelashes and the contour of the eyes.

Thus, the glossy appearance is conventionally afforded, in a cosmetic composition of lip gloss type, by the use of oily fatty substances, and in a composition of varnish type, by the use of rigid film-forming polymers.

However, the use of these two types of compound that are efficient for forming a glossy film impairs the drying properties as regards the oils and the comfort as regards the rigid film-forming polymers. Specifically, in the presence of oily fatty substances, the film deposited on the keratin materials does not dry, and the use of rigid film-forming polymers makes the deposit uncomfortable to users due to the perceived rigidity.

DETAILED DESCRIPTION

The need thus remains for compositions, especially cosmetic compositions, especially mascaras and eyeliners, which have, after application, a long-lasting glossy makeup result, while at the same time remaining capable of presenting good properties in terms of transfer resistance, comfort, residual tack resistance and persistence over time.

Contrary to all expectations, the inventors have found that a combination of at least one hydrocarbon-based oil as defined below, of at least specific particles of at least one stabilized polymer as defined below and of at least one specific hydrophobic film-forming polymer as defined below makes it possible precisely to satisfy this need.

Thus, according to a first of its aspects, the present invention relates to a composition, especially a cosmetic composition, for caring for and/or making up keratin materials, especially the eyelashes, comprising at least:

a non-aqueous medium containing at least one hydrocarbon-based oil, particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; and a hydrophobic film-forming polymer chosen from block ethylenic copolymers and hydrocarbon-based resins, and mixtures thereof.

According to an advantageous variant, said particles are in dispersion in said non-aqueous medium containing at least one hydrocarbon-based oil.

Contrary to all expectations, and as demonstrated in the experimental section below, the inventors have in fact found that the presence of at least one hydrocarbon-based oil as defined below, of at least specific particles of at least one stabilized polymer as defined below, and of at least one specific hydrophobic film-forming polymer as defined below makes it possible to gain access to a mascara formulation or to a liner formulation which retains expected properties in terms of persistence, although containing a vehicle, and which advantageously makes it possible to obtain a glossy, long-lasting, transfer-resistant deposit which has no residual tack and which is comfortable.

The compositions according to the invention may especially be makeup compositions intended for affording the desired makeup effect, by their use alone on the eyelashes, but may also be non-pigmented or coloured compositions intended either to be superimposed on makeup already deposited on the eyelashes or to be coated with a related makeup film: they are then teamed, respectively, a top coat or a base coat. They may also be compositions intended for affording only care on keratin fibres and in particular the eyelashes.

The compositions according to the invention also find another advantageous application in the field of liners and more particularly of eyeliners.

According to another of its aspects, a subject of the invention is also a process, especially a cosmetic process, for making up and/or caring for keratin materials, especially the eyelashes, comprising at least one step which consists in applying to said keratin materials a composition in accordance with the invention.

The present invention is also directed towards the use of a dispersion of particles of at least one polymer that is surface-stabilized with a stabilizer in a non-aqueous medium containing at least one hydrocarbon-based oil, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth) acrylate/$C_1$-$C_4$ alkyl (meth)acrylate weight ratio of greater than 4, for preparing a mascara or eyeliner composition.

Hydrophobic Film-Forming Polymers

As stated previously, a composition according to the invention comprises at least one hydrophobic film-forming polymer.

A hydrophobic film-forming polymer that is suitable for use in the invention is chosen from block ethylenic copolymers and hydrocarbon-based resins, and mixtures thereof.

1. Block Ethylenic Copolymers

According to a particular embodiment of the invention, the hydrophobic film-forming polymer is a block ethylenic copolymer, containing at least a first block with a glass transition temperature ($T_g$) of greater than or equal to 40° C.

and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., said first block and said second block being connected together via a statistical intermediate segment comprising at least one of said first constituent monomers of the first block and at least one of said second constituent monomers of the second block, and said block copolymer having a polydispersity index 1 of greater than 2.

Polymers of this type that are suitable for use in the invention are described in document EP 1 411 069.

As examples of such polymers, mention may be made more particularly of Mexomere PAS® (acrylic acid/isobutyl acrylate/isobornyl acrylate copolymer 50% diluted in isododecane) sold by the company Chimex.

The block ethylenic copolymer(s) may be present in a content ranging from 5% to 50% by weight, preferably ranging from 5% to 40% by weight and even more advantageously from 8% to 30% by weight, relative to the total weight of the composition.

2. Hydrocarbon-Based Resins:

As stated previously, the claimed compositions may comprise at least one hydrocarbon-based resin, especially as detailed hereinbelow.

The hydrocarbon-based resins are preferably chosen from low molecular weight polymers that may be classified, according to the type of monomer they comprise, as:

indene hydrocarbon-based resins, preferably such as resins derived from the polymerization in major proportion of indene monomer and in minor proportion of a monomer chosen from styrene, methylindene and methylstyrene, and mixtures thereof. These resins may optionally be hydrogenated. These resins may have a molecular weight ranging from 290 to 1,150 g/mol.

Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp., or the hydrogenated indene/methylstyrene/styrene copolymers sold under the name "Regalite" by the company Eastman. Chemical, in particular Regalite R 1100, Regalite R 1090, Regalite R-7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomer(s) chosen from isoprene, butene, 2-methyl-2-butene, pentene and 1,4-pentanediene, and mixtures thereof. These resins may have a molecular weight ranging from 1,000 to 2,500 g/mol.

Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentanediene dimers such as those derived from the polymerization of a first monomer chosen from indene and styrene, and of a second monomer chosen from cyclopentanediene dimers such as dicyclopentanediene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, α-pinene and limonene, and mixtures thereof. These resins may have a molecular weight ranging from 300 to 2000 g/mol. Such resins are sold, for example, under the names Piccolyte A115 and S125 by Hercules or Zonarez 7100 or Zonatac 105 Lite by Arizona Chem.

According to a preferred embodiment, the hydrocarbon-based resin is chosen from hydrocarbon-based resins that are solid at room temperature (20° C.).

According to a preferred embodiment, the hydrocarbon-based resin is chosen from indene hydrocarbon-based resins, aliphatic pentadiene resins, mixed resins of pentanediene and of indene, diene resins of cyclopentanediene dimers and diene resins of isoprene dimers, and mixtures thereof.

Preferably, the composition comprises at least one compound chosen from hydrocarbon-based resins as described previously, especially from indene hydrocarbon-based resins and aliphatic pentadiene resins, and mixtures thereof. According to one preferred embodiment, the hydrocarbon-based resin is chosen from indene hydrocarbon-based resins.

According to a preferred embodiment, the resin is chosen from hydrogenated indene/methylstyrene/styrene copolymers.

In particular, use may be made of hydrogenated indene/methylstyrene/styrene copolymers, such as those sold under the name Regalite by the company Eastman Chemical, such as Regalite R 1100 CG Hydrocarbon Resin, Regalite R 1100, Regalite R 1090, Regalite R-7100, Regalite R1010 Hydrocarbon Resin and. Regalite R1125 Hydrocarbon Resin.

A composition according to the invention may comprise from 5% to 50% by weight, preferably from 5% to 45% by weight and even more preferentially from 8% to 40% by weight of hydrocarbon-based resin(s) relative to the total weight of the composition.

Hydrocarbon-Based Oil

The composition according to the invention comprises a hydrocarbon-based oil.

This oil may be volatile (vapour pressure greater than or equal to 0.13 Pa measured at 25° C.) or non-volatile (vapour pressure less than 0.13 Pa measured at 25° C.).

Preferably, the hydrocarbon-based oil is volatile.

The hydrocarbon-based oil is an oil (non-aqueous compound) that is liquid at room temperature (25° C.).

The term "hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from:

hydrocarbon-based oils containing from 8 to 16 carbon atoms, and especially:
- branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl,
- linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof,
- short-chain esters (containing from 3 to 8 carbon atoms in total) such as ethyl acetate, methyl acetate, propyl acetate or n-butyl acetate,
- hydrocarbon-based oils of plant origin such as triglycerides constituted by fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel,
- synthetic ethers containing from 10 to 40 carbon atoms;
- linear or branched hydrocarbons of mineral or synthetic origin, such as petroleum jelly, polydecenes, hydrogenated polyisobutene such as Parleam®, squalane and liquid paraffins, and mixtures thereof,
- synthetic esters such as oils of formula $R_1COOR_2$ in which $R_1$ represents a linear or branched fatty acid residue containing from 1. to 40 carbon atoms and $R_2$ represents an, in particular, branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
- fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, mixtures thereof.

More particularly, the content of hydrocarbon-based oil(s) ranges from 30% to 75% by weight and preferably from 40% to 60% by weight relative to the total weight of the composition.

This hydrocarbon-based oil may be provided totally or partly with the surface-stabilized polymer particles, in particular when these particles are introduced into the composition in the form of a pre-prepared dispersion of stabilized polymer particles. In this case, the hydrocarbon-based oil present in the composition represents at least the non-aqueous medium of the dispersion of polymer particles.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms and better still from 12 to 16 carbon atoms, in particular the apolar oils described previously.

Preferentially, the hydrocarbon-based oil is isododecane. More particularly, the isododecane content ranges from 30% to 70% by weight, preferably from 35% to 65% by weight and even more preferentially from 40% to 60% by weight relative to the total weight of the composition.

Preferably, the hydrocarbon-based oil(s), in particular isododecane, constitute the only oil(s) of the composition, or are present in a predominant weight content relative to the additional oil(s) that may be present in the composition.

Thus, according to a particular embodiment, the hydrocarbon-based oil(s) are present in a composition according to the invention In a content ranging from 30% to 70% by weight, preferably from 35% to 65% by weight and even more preferentially from 40% to 60% by weight relative to the total weight of the composition, the hydrocarbon-based oil(s) preferably being apolar, more preferentially volatile, even more preferentially containing from 8 to 16 carbon atoms, or even better still isododecane.

In accordance with a particular embodiment of the invention, if the composition contains one or more non-volatile oils, their content advantageously does not exceed 10% by weight, preferably does not exceed 5% by weight relative to the total weight of the composition, and better still is less than 2% by weight relative to the total weight of the composition, or even is free of non-volatile oil(s).

Polymer Particles

The composition according to the invention moreover comprises particles, which are generally spherical, of at least one surface-stabilized polymer.

Preferably, the particles are introduced into the composition in the form of a dispersion of particles, which are generally spherical, of at least one surface-stabilized polymer, in an oily medium, advantageously containing at least one hydrocarbon-based oil, as defined previously.

The polymer of the particles is a $C_1$-$C_4$ alkyl (meth)acrylate polymer.

The $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and Cert-butyl (meth)acrylate.

A $C_1$-$C_4$ alkyl acrylate monomer is advantageously used. Preferentially, the polymer of the particles is a methyl acrylate and/or ethyl acrylate polymer.

The polymer of the particles may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminium, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of 80% to 100% by weight of $C_1$-$C_4$ alkyl (meth)acrylate and of 0 to 20% by weight of ethylenically unsaturated acid monomer, relative to the total weight of the polymer.

According to a first embodiment of the invention, the polymer consists essentially of a polymer of one or more $C_1$-$C_4$ alkyl (meth)acrylate monomers.

According to a second embodiment of the invention, the polymer consists essentially of a copolymer of $C_1$-$C_4$ (meth) acrylate and of (meth)acrylic acid or maleic anhydride.

The polymer of the particles may be chosen from:
methyl acrylate homopolymers
ethyl acrylate homopolymers
methyl acrylate/ethyl acrylate copolymers
methyl acrylate/ethyl acrylate/acrylic acid copolymers
methyl acrylate/ethyl acrylate/maleic anhydride copolymers
methyl acrylate/acrylic acid copolymers
ethyl acrylate/acrylic acid copolymers
methyl acrylate/maleic anhydride copolymers
ethyl acrylate/maleic anhydride copolymers.

Advantageously, the polymer of the particles is a non-crosslinked polymer.

The polymer of the particles preferably has a number-average molecular weight ranging from 2000 to 10 000 000 and preferably ranging from 150 000 to 500 000.

In the case of a particle dispersion, the polymer(s) of the particles may be present in the dispersion in a content ranging from 21% to 58.5% by weight and preferably ranging from 36% to 42% by weight, relative to the total weight of the dispersion. The stabilizer is an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, preferably greater than 4.5 and even more advantageously greater than or equal to 5. Advantageously, said weight ratio ranges from 4.5 to 19, preferably from 5 to 19 and more particularly from 5 to 12.

Thus, according to a particular embodiment, a composition according to the invention comprises one or more stabilizers, said stabilizer(s) being a statistical copolymer of isobornyl (meth)acrylate and of $C_1$-$C_4$ alkyl (meth)acrylate present in an isobornyl (meth)acrylate/$C_1$-$C_4$ alkyl (meth) acrylate weight ratio of greater than or equal to 5.

Advantageously, the stabilizer is chosen from:
isobornyl acrylate homopolymers
statistical copolymers of isobornyl acrylate/methyl acrylate
statistical copolymers of isobornyl acrylate/methyl acrylate/ethyl acrylate
statistical copolymers of isobornyl methacrylate/methyl acrylate
in the weight ratio described previously.

The stabilizing polymer preferably has a number-average molecular weight ranging from 10 000 to 400 000 and preferably ranging from 20 000 to 200 000.

The stabilizer is in contact with the surface of the polymer particles and thus makes it possible to stabilize these particles at the surface, in particular in order to keep these particles in dispersion in the non-aqueous medium of the dispersion.

Advantageously, the combination of the stabilizer(s)+polymer(s) of the particles present in particular in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer(s)+polymer(s) of the particles.

Preferentially, the combination of the stabilizer(s)+polymer(s) of the particles present in particular in the dispersion comprises from 15% to 30% by weight of polymerized isobornyl (meth)acrylate and from 70% to 85% by weight of polymerized $C_1$-$C_4$ alkyl (meth)acrylate, relative to the total weight of the combination of the stabilizer(s) polymer(s) of the particles.

Preferably, the stabilizer(s) are soluble in the hydrocarbon-based oil(s), in particular soluble in isododecane.

According to a theory which should not limit the scope of the present invention, the inventors put forward the hypothesis that the surface stabilization of the $C_1$-$C_4$ alkyl (meth)acrylate polymer particles results from a phenomenon of surface adsorption of the stabilizer onto the $C_1$-$C_4$ alkyl (meth)acrylate polymer particles.

When the polymer particles are provided in the composition in the form of a pre-prepared dispersion, the oily medium of this polymer dispersion comprises a first hydrocarbon-based oil. Reference may be made to that which has been indicated previously concerning this oil as regards its nature.

Advantageously, the hydrocarbon-based oil is apolar and preferably chosen from hydrocarbon-based oils containing from 8 to 16 carbon atoms, in particular the apolar oils described previously.

Preferentially, the hydrocarbon-based oil is isododecane.

The polymer particles, in particular in the dispersion, preferably have an average size, especially a number-average size, ranging from 50 to 500 nm, especially ranging from 75 to 400 nm and better still ranging from 100 to 250 nm.

In general, a dispersion of polymer particles that is suitable for use in the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer, with a radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with said synthesis solvent) and selectively distilling off the synthesis solvent.

A synthesis solvent which is such that the monomers of the stabilizing polymer and the radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in said oil, which thus also acts as synthesis solvent. The monomers should also be soluble therein, as should the radical initiator, and the polymer of the particles obtained should be insoluble therein.

The monomers are preferably present in the synthesis solvent, before polymerization, in a proportion of 5%-20% by weight. The total amount of the monomers may be present in the solvent before the start of the reaction, or part of the monomers may be added gradually as the polymerization reaction proceeds.

The radical initiator may especially be azobisisobutyronitrile or tert-butyl peroxy-2-ethylhexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer particle dispersion advantageously comprises from 30% to 65% by weight and preferably from 40% to 60% by weight of solids, relative to the total weight of the dispersion.

A composition according to the invention may thus comprise from 5% to 50% by weight, preferably from 8% to 45% by weight and more preferentially from 10% to 30% by weight of polymer particles as described previously, relative to the total weight of the composition (content expressed as solids).

Aqueous Phase

The aqueous phase of a composition according to the invention comprises water and optionally a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

Among the water-soluble solvents that may be used in the composition in accordance with the invention, mention may be made especially of lower monoalcohols containing from 1 to 5 carbon atoms such as ethanol and isopropanol, glycols containing from 2 to 8 carbon atoms such as ethylene glycol, propylene glycol, 1,3-butylene glycol and dipropylene glycol, $C_3$ and $C_4$ ketones and $C_2$-$C_4$ aldehydes.

According to another embodiment variant, the aqueous phase of a composition according to the invention may comprise at least one $C_2$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at room temperature.

Such polyols may be used in a proportion ranging from 0.2% to 10% by weight, preferably from 0.5% to 8% by weight and even more preferentially from 0.5% to 6% by weight of $C_2$-$C_{32}$ polyol relative to the total weight of the composition.

The polyols that are advantageously suitable for the formulation of a composition according to the present invention are those especially containing from 2 to 32 carbon atoms, preferably from 3 to 16 carbon atoms and in particular from 3 to 7 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols such as glycerol oligomers, for instance diglycerol, and polyethylene glycols, and mixtures thereof, in particular pentylene glycol.

According to a preferred embodiment of the invention, said polyol is chosen from ethylene glycol, pentaerythritol, trimethylolpropane, propylene glycol, pentylene glycol, glycerol, polyglycerols and polyethylene glycols, and mixtures thereof.

According to a particular mode, the composition of the invention may comprise at least pentylene glycol.

According to one particular embodiment, a composition according to the invention is anhydrous.

For the purposes of the invention, a composition is said to be anhydrous when it comprises less than 5% by weight of water, better still less than 2% by weight of water, or even less than 1% by weight of water relative to the total weight of the composition, and is especially free of water. Where appropriate, such small amounts of water may especially be introduced by ingredients of the composition that may contain residual amounts thereof.

Waxes

For the purposes of the present invention, the term "wax" means a lipophilic fatty compound that is solid at room temperature (25° C.), with a reversible solid/liquid change of state, having a melting point of greater than 30° C. which may be up to 200° C., a hardness of greater than 0.5 MPa, and having an anisotropic crystal organization in the solid state. By bringing the wax to its melting point, it is possible to make it miscible with oils and to form a microscopically homogeneous mixture, but on returning the temperature of the mixture to room temperature, recrystallization of the wax in the oils of the mixture is obtained.

The waxes that may be used in the invention are compounds that are solid at room temperature, which are intended to structure the composition, in particular in stick form; they may be hydrocarbon-based and/or silicone-based and may be of plant, mineral and/or synthetic origin. In particular, they have a melting point of greater than 40° C. and better still greater than 45° C.

As waxes that may be used in the invention, mention may be made of those generally used in cosmetics: they are especially of natural origin, such as beeswaxes, carnauba wax, especially such as the product sold under the name Cerauba T1 by the company Baerlocher, candelilla wax, ouricury wax, Japan wax, cork fibre wax or sugarcane wax, rice wax, montan wax, paraffin waxes especially such as the product sold under the name Affine 56-58 Pastilles by the company Baerlocher, lignite wax or microcrystalline wax, ceresin or ozokerite, hydrogenated waxes such as jojoba oil; synthetic waxes such as polyethylene waxes derived from the polymerization or copolymerization of ethylene and. Fischer-Tropsch waxes, or alternatively fatty acid esters such as octacosanyl stearate, glycerides that are concrete at 40° C. and better still at 45° C., silicone waxes such as alkyl or alkoxy dimethicones with an alkyl or alkoxy chain of 10 to 45 carbon atoms, poly(di)methylsiloxane esters that are solid at 40° C., the ester chain of which comprises at least 10 carbon atoms; and mixtures thereof.

Preferably, the composition according to the invention comprises less than 10% by weight of wax(es), in particular less than 5% by weight of wax(es), relative to the total weight of the composition, and more particularly is free of wax.

Pasty Compound

For the purposes of the present invention, the term "pasty" is intended to denote a lipophilic fatty compound with a reversible solid/liquid change of state, and comprising at a temperature of 25° C. a liquid fraction and a solid fraction.

A pasty compound is advantageously chosen from:
lanolin and derivatives thereof,
petroleum jelly,
polyol ethers,
polymeric or non-polymeric silicone compounds,
liposoluble polyethers resulting from polyetherification between one or more $C_2$-$C_{100}$ and preferably $C_2$ $C_{50}$ diols,
esters such as esters of a glycerol oligomer, arachidyl propionate, phytosterol esters, fatty acid triglycerides and derivatives thereof, pentaerythritol esters, esters of a diol dimer and a diacid dimer, mango butter, shea butter, and mixtures thereof,
and mixtures thereof.

Preferably, the composition according to the invention comprises less than 10% by weight of pasty compound, in particular less than 5% by weight of pasty compound, relative to the total weight of the composition, and more particularly the composition is free of pasty compound.

Dyestuffs

The compositions in accordance with the invention may comprise at least one dyestuff.

This (or these) dyestuff(s) are preferably chosen from pulverulent substances, liposoluble dyes and water-soluble dyes, and mixtures thereof Preferably, the compositions according to the invention comprise at least one pulverulent dyestuff. The pulverulent dyestuffs may be chosen from pigments and nacres, and preferably from pigments.

The pigments may be white or coloured, mineral and/or organic, and coated or uncoated. Among the mineral pigments, mention may be made of metal oxides, in particular titanium dioxide, optionally surface-treated, zirconium, zinc or cerium oxides, and also iron, titanium or chromium oxides, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides. More preferentially, the pigments contained in the compositions according to the invention are chosen from iron oxides, such as especially those sold under the name Sunpuro Black Iron Oxide C33-7001® by the company Sun.

Thus, according to a particular embodiment, a composition according to the invention also comprises at least one dyestuff, the dyestuff(s) preferably being chosen from pulverulent materials, in particular pigments, more particularly from metal oxides such as iron oxides.

These dyestuffs may be present in a content ranging from 0.01% to 30% by weight relative to the total weight of the composition and in particular from 1% to 22% by weight relative to the total weight of the composition.

Preferably, the dyestuff(s) are chosen from one or more metal oxides that are present in a content of greater than or equal to 1% by weight relative to the total weight of the composition, and advantageously inclusively between 3% and 22% by weight relative to the total weight of the composition.

Additives

The compositions according to the invention may also comprise any cosmetic active agent, such as active agents chosen from an additional volatile or non-volatile silicone oil, fibres, fillers, antioxidants, preserving agents, fragrances, bactericidal active agents, neutralizers, emollients, moisturizers, trace elements, softeners, sequestrants, acidifying or basifying agents, hydrophilic or lipophilic active agents, coalescers and vitamins, and mixtures thereof.

Among the thickeners, examples that may be mentioned include hydrocarbon-based block copolymers that are suited to mascara composition formulations.

The hydrocarbon-based block copolymers that are suitable for use in the invention, also known as block copolymers, are preferably soluble or dispersible in the oily phase.

The hydrocarbon-based block copolymer may especially be a diblock copolymer.

Such hydrocarbon-based block copolymers are described in patent application US-A-2002/005562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of said block may be between −150° C. and 20° C. and especially between −100° C. and 0° C.

The hydrocarbon-based block copolymer present in the composition according to the invention may be an amorphous copolymer formed by polymerization of an olefin. The olefin may especially be an elastomeric ethylenically unsaturated monomer.

The term "amorphous polymer" means a polymer that does not have a crystalline form.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the hydrocarbon-based block copolymer is an amorphous block copolymer of styrene and of an olefin.

Block copolymers comprising at least one styrene block and at least one block comprising units chosen from butadiene, ethylene, propylene, butylene and isoprene or a mixture thereof are especially preferred.

According to one preferred embodiment, the hydrocarbon-based block copolymer is hydrogenated to reduce the residual ethylenic unsaturations after the polymerization of the monomers.

In particular, the hydrocarbon-based block copolymer is an optionally hydrogenated copolymer, containing styrene blocks and ethylene/$C_3$-$C_4$ alkylene blocks.

According to one preferred embodiment, the composition according to the invention comprises at least one diblock copolymer, which is preferably hydrogenated, preferably chosen from styrene-ethylene/propylene copolymers, styrene-ethylene/butadiene copolymers and styrene-ethylene/butylene copolymers. Diblock polymers are especially sold under the name Kraton® G1701E by the company Kraton Polymers.

A diblock copolymer such as those described above, in particular a styrene-ethylene/propylene diblock copolymer, is advantageously used as hydrocarbon-based block copolymer.

The hydrocarbon-based block copolymer(s) may be present in a content ranging from 0.5% to 15% by weight, relative to the total weight of the composition, preferably ranging from 1% to 10% by weight and even more advantageously from 2% to 8% by weight, relative to the total weight of the composition.

It is a matter of routine operations for a person skilled in the art to adjust the nature and the amount of the additives present in the compositions in accordance with the invention such that the desired cosmetic properties thereof are not thereby affected.

According to a preferred embodiment, a composition of the invention is in the form of a product for the eyelashes, in particular a mascara.

According to another embodiment, a composition of the invention may advantageously be in the form of a product for the eyebrows.

Preferably, a composition according to the invention is in the form of a composition for caring for and/or making up keratin fibres, in particular the eyelashes, preferably in the form of a mascara.

According to another preferred embodiment, a composition of the invention is in the form of a product for the contour of the eyes or the eyelids, in particular a liner such as an eyeliner.

Preferably, a composition according to the invention is in the form of a composition for caring for and/or making up keratin materials, in particular for the contour of the eyes or the eyelids, preferably in the form of a liner.

Such compositions are especially prepared according to the general knowledge of a person skilled in the art.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

In the description and the examples, the percentages are percentages by weight, unless otherwise indicated. The percentages are thus given on a weight basis relative to the total weight of the composition. The ingredients are mixed in the order and under the conditions that are easily determined by those skilled in the art.

I. EXAMPLES OF PREPARATION OF DISPERSIONS

Example 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated to 90° C. under argon with. stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 litres of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate. The polymer particles of the dispersion have a number-average size of about 160 nm.

The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 litres of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained. The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 litre of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 litre of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

II. COMPOSITION EXAMPLES: MASCARAS OR LINERS

The formulation of composition 1 (corresponding to a mascara) in accordance with the invention is prepared as described below: The components are weighed out in a heating pan and stirred with a Rayneri blender, at 90-95° C.

Once the gel has been prepared and is homogeneous, the mixture returns to room temperature with stirring using the Rayneri blender (25° C.).

The formulations (corresponding to a liner) in accordance with the invention (compositions 2 to 4) or not in accordance with the invention (compositions 5 and 6) are prepared as described below.

The components are weighed out in a heating pan and stirred with a Rayneri blender, at room temperature (25° C.) until the mixture is homogeneous.

| Compounds | Mascara composition 1 according to the invention | Eyeliner composition 2 according to the invention | Eyeliner composition 3 according to the invention |
|---|---|---|---|
| (Methyl acrylate)-co-(isobornyl acrylate) (80.7/19.3) copolymer dissolved in isododecane according to Preparation Example 1 described previously | 44.64% | 38.70% | 50.00% |
| Hydrogenated styrene/isoprene copolymer (Kraton G1701 EU ® sold by the company Kraton Polymers) | 7.44% | — | — |
| Hydrogenated styrene/methylstyrene/indene copolymer (Regalite R1100 | 14.88% | — | — |

-continued

| Compounds | | | |
|---|---|---|---|
| CG Hydrocarbon Resin ® sold by the company Eastman Chemical) | | | |
| Acrylic acid/isobutyl acrylate/isobornyl acrylate copolymer (Mexomer PAS ® sold by the company Chimex) | — | 38.70% | 50.00% |
| Acrylates/polytrimethylsiloxy methacrylate copolymer (Dow Corning FA 4002 ID Silicone Acrylate ® sold by the company Dow Corning) | — | — | — |
| Polybutene (Indopol H 1500 ® sold by the company Ineos) | — | — | — |
| Iron oxides/CI 77499 (Sunpuro Black Iron Oxide C33-7001 ® sold by the company Sun) | 7.00% | 10.00% | — |
| Phenoxyethanol (Sepicide LD ® sold by the company SEPPIC) | 0.50% | 0.45% | — |
| Pentylene glycol (616751 Hydrolite ®-5 sold by the company Symrise) | — | 2.70% | — |
| Isododecane sold by the company Ineos | qs 100 | qs 100 | — |

| Compounds | Eyeliner composition 4 according to the invention | Eyeliner composition 5 outside the invention | Eyeliner composition 6 outside the invention |
|---|---|---|---|
| (Methyl acrylate)-co-(isobornyl acrylate) (80.7/19.3) copolymer dissolved in isododecane according to Preparation Example 1 described previously | 50.00% | 50.00% | 50.00% |
| Hydrogenated styrene/isoprene copolymer (Kraton G1701 EU ® sold by the company Kraton Polymers) | — | — | — |
| Hydrogenated styrene/methylstyrene/indene copolymer (Regalite R1100 CG Hydrocarbon Resin ® sold by the company Eastman Chemical) | 30.00% | — | — |
| Acrylic acid/isobutyl acrylate/isobornyl acrylate copolymer (Mexomer PAS ® sold by the company Chimex) | — | — | — |
| Acrylates/polytrimethylsiloxy methacrylate copolymer (Dow Corning FA 4002 ID Silicone Acrylate ® sold by the company Dow Corning) | — | 20.00% | — |
| Polybutene (Indopol H 1500 ® sold by the company Ineos) | — | — | 50.00% |
| Iron oxides/CI 77499 (Sunpuro Black Iron Oxide C33-7001 ® sold by the company Sun) | — | — | — |
| Phenoxyethanol (Sepicide LD ® sold by the company SEPPIC) | — | — | — |
| Pentylene glycol (616751 Hydrolite ®-5 sold by the company Symrise) | — | — | — |
| Isododecane sold by the company Ineos | qs 100 | qs 100 | — |

Measurement of the Gloss and of the Residual Tack

Protocol for Measuring the Gloss of a Composition

The gloss of compositions 1 to 6 was measured using a Byk spectro-guide sphere gloss glossmeter.

Principle of the Measurement Using this Glossmeter

The machine illuminates the sample to be analysed at a certain incidence and measures the intensity of the specular reflection.

The intensity of the reflected light depends on the material and on the angle of illumination. For non-ferrous materials (paint, plastic), the intensity of reflected light increases with the angle of illumination. The rest of the incident light penetrates the material and, depending on the shade of the colour, is either partly absorbed or scattered.

The reflectometer measurement results are not based on the amount of incident light but on a polished black glass standard of defined refractive index.

The measurement is normalized relative to an internal standard and brought to a value out of 100: For this calibration standard, the measurement value is set at 100 gloss units (calibration).

The closer the measured value is to 100, the more glossy the sample. The measurement unit is the Gloss Unit (GU).

The angle of illumination used has a strong influence on the reflectometer value. In order to be able to readily differentiate very glossy and matt surfaces, the standardization has defined three geometries or three measurement domains.

Test Protocol a—Spread a coat with a wet thickness of 300 μm of the composition whose mean gloss value it is desired to evaluate onto a Leneta brand contrast card of reference Form 1A Penopac, using an automatic spreader. The coat covers the white background and the black background of the card.

b—Leave to dry for 24 hours at 37° C.

c—Measure the gloss at 60° on the white matt absorbent background (3 measurements) using a Byk Gardner brand glossmeter of reference spectro-guide sphere gloss.

The measured values in. GU obtained for the various test compositions should then be compared. The lower the value measured, the more matt the deposit.

Protocol for Measuring the Residual Tack

The tack is evaluated by feel. A film with a wet thickness of 300 μm is produced on a glass plate using an automatic spreader. The film is left to dry in an oven at 37° C. for 24 hours. After these 24 hours, the tack is evaluated by touching the film with a. finger.

Results

The results are recapitulated in the table below.

| Measurements | Composition 1 according to the invention | Composition 2 according to the invention | Composition 3 according to the invention |
|---|---|---|---|
| Gloss measured at 60° on a contrast card | 81 | 75 | 86.7 ± 1.5 |
| Gloss measured at 60° on a glass plate | Not measured | Not measured | 130 ± 2.6 |
| Residual tack on touching | None | None | None |

| Measurements | Composition 4 according to the invention | Composition 5 outside the invention | Composition 6 outside the invention |
|---|---|---|---|
| Gloss measured at 60° on a contrast card | 90.31 ± 1.8 | 54.2 ± 3.2 | Not measured |
| Gloss measured at 60° on a glass plate | 118.8 ± 4.6 | 77.9 ± 1.2 | 13.5 ± 2.3 |
| Residual tack on touching | Low | None | Very high |

The deposit of compositions 1 to 4 according to the invention is glossy and presents little or no residual tack on touching. Furthermore, compositions 1 to 4 in accordance with the invention have good properties in terms of transfer resistance and persistence.

As regards the deposit of compositions 5 and 6 not in accordance with the invention, the absence of hydrophobic film-forming polymer suitable for use in the invention results in a significant loss of gloss and also, for one of the two compositions (composition 6), the residual tack on touching is very high.

The invention claimed is:

1. A composition for caring for and/or making up keratin materials, comprising at least:
   a non-aqueous medium containing at least one hydrocarbon-based oil,
   particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; and
   a hydrophobic film-forming polymer chosen from block ethylenic copolymers and hydrocarbon-based resins, and mixtures thereof,
   wherein
   the block ethylenic polymer is an acrylic acid/isobutyl acrylate/isobornyl acrylate copolymer;
   wherein the hydrocarbon-based resin is chosen from indene hydrocarbon-based resins, aliphatic pentadiene resins, mixed resins of pentanediene and of indene, diene resins of cyclopentanediene dimers, diene resins of isoprene dimers and mixtures thereof.

2. The composition according to claim 1, wherein said particles are in dispersion in said non-aqueous medium containing at least one hydrocarbon-based oil.

3. The composition according to claim 1, wherein the hydrocarbon-based oil(s) are present in a composition according to the invention in a content ranging from 30% to 70% by weight relative to the total weight of the composition, the hydrocarbon-based oil(s) being apolar.

4. The composition according to claim 1, wherein the polymer(s) of the particles are present in an amount ranging from 5% to 50% by weight relative to the total weight of the composition.

5. The composition according to claim 1, wherein the polymer(s) of the particles is a (are) methyl acrylate and/or ethyl acrylate polymer(s).

6. The composition according to claim 1, wherein the polymer(s) of the particles comprise an ethylenically unsaturated acid monomer or the anhydride thereof.

7. The composition according to claim 1, wherein the polymer(s) of the particles comprise from 80% to 100% by weight of $C_1$-$C_4$ alkyl (meth)acrylate and from 0% to 20% by weight of ethylenically unsaturated acid monomer, relative to the total weight of the polymer, the polymer(s) of the particles being chosen from:
   methyl acrylate homopolymers
   ethyl acrylate homopolymers
   methyl acrylate/ethyl acrylate copolymers
   methyl acrylate/ethyl acrylate/acrylic acid copolymers
   methyl acrylate/ethyl acrylate/maleic anhydride copolymers
   methyl acrylate/acrylic acid copolymers
   ethyl acrylate/acrylic acid copolymers
   methyl acrylate/maleic anhydride copolymers
   ethyl acrylate/maleic anhydride copolymers.

8. The composition according to claim 1, wherein the stabilizer(s) is a (are) statistical copolymer(s) of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than or equal to 5.

9. The composition according to claim 1, wherein the stabilizer(s) are chosen from:
   isobornyl acrylate homopolymers
   statistical copolymers of isobornyl acrylate/methyl acrylate
   statistical copolymers of isobornyl acrylate/methyl acrylate/ethyl acrylate
   statistical copolymers of isobornyl methacrylate/methyl acrylate.

10. The composition according to claim 1, wherein the combination of the stabilizer(s) +polymer(s) of the particles present in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer(s) +polymer(s) of the particles.

11. The composition according to claim 1, wherein the composition comprises less than 5% by weight of water relative to the total weight of the composition.

12. The composition according to claim 1, wherein the block ethylenic copolymer(s) are present in a content ranging from 5% to 50% by weight relative to the total weight of the composition.

13. The composition according to claim 1, wherein the hydrocarbon-based resin(s) are present in a content ranging from 5% to 50% by weight relative to the total weight of the composition.

14. The composition according to claim 1, further comprising at least one dyestuff.

* * * * *